(12) United States Patent
Bock et al.

(10) Patent No.: US 9,505,711 B2
(45) Date of Patent: Nov. 29, 2016

(54) METHOD FOR PURIFYING MIXTURES COMPRISING 4,4'-METHYLENEDIPHENYL DIISOCYANATE

(75) Inventors: Michael Bock, Ruppertsberg (DE); Johannes Jacobs, Antwerpen (BE); Kai Thiele, Antwerpen (BE); Anne-Kathrin Merten, Lauchhammer (DE)

(73) Assignee: BASF SE, Ludwigshafen (DE)

( * ) Notice: Subject to any disclaimer, the term of this patent is extended or adjusted under 35 U.S.C. 154(b) by 160 days.

(21) Appl. No.: 13/296,665

(22) Filed: Nov. 15, 2011

(65) Prior Publication Data

US 2012/0142960 A1  Jun. 7, 2012

Related U.S. Application Data

(60) Provisional application No. 61/414,446, filed on Nov. 17, 2010.

(51) Int. Cl.
*C07C 249/00* (2006.01)
*C07C 263/20* (2006.01)

(52) U.S. Cl.
CPC .................................. *C07C 263/20* (2013.01)

(58) Field of Classification Search
CPC . C07C 265/10; C07C 263/18; C07C 263/10; C07C 265/12; C07C 263/20; C07C 263/16; C07C 273/1809; C07C 265/14; C08G 18/758
USPC .................................. 560/330, 347, 336, 352
See application file for complete search history.

(56) References Cited

U.S. PATENT DOCUMENTS

| | | | | |
|---|---|---|---|---|
| 3,410,888 | A | * | 11/1968 | Hammond ..................... 560/347 |
| 4,189,354 | A | * | 2/1980 | Ellendt et al. .................. 203/81 |
| 4,385,171 | A | * | 5/1983 | Schnabel et al. .............. 528/491 |
| 4,414,074 | A | * | 11/1983 | Ellendt ................. C07C 263/20 203/21 |
| 2009/0292098 | A1 | * | 11/2009 | Wagner et al. ................. 528/48 |
| 2011/0144381 | A1 | | 6/2011 | Doerr et al. |
| 2011/0263892 | A1 | | 10/2011 | Breuninger et al. |
| 2012/0046497 | A1 | | 2/2012 | Stroefer et al. |
| 2012/0101299 | A1 | | 4/2012 | Schelling et al. |
| 2012/0253063 | A1 | | 10/2012 | Mattke et al. |

FOREIGN PATENT DOCUMENTS

| | | |
|---|---|---|
| CN | 101003497 A | 7/2007 |
| DE | 1 923 214 | 11/1970 |
| DE | 26 31 168 A1 | 1/1978 |
| DE | 29 33 601 C2 | 3/1981 |
| DE | 31 45 010 A1 | 5/1983 |
| DE | 288 599 A5 | 4/1991 |
| DE | 103 33 929 A1 | 2/2005 |
| DE | 10 2005 004 170 A1 | 8/2006 |
| DE | 10 2005 055 189 A1 | 5/2007 |
| EP | 1 475 367 A1 | 11/2004 |
| GB | 798636 A | 7/1958 |
| GB | 1384065 | * 2/2013 |
| WO | WO 2010/057909 A1 | 5/2010 |
| WO | WO 2010/121997 A1 | 10/2010 |
| WO | WO 2010/149544 A2 | 12/2010 |
| WO | WO 2011/058069 A2 | 5/2011 |
| WO | WO 2011/067369 A1 | 6/2011 |
| WO | WO 2012/065927 A1 | 5/2012 |
| WO | WO 2012/065995 A1 | 5/2012 |
| WO | WO 2012/066001 A1 | 5/2012 |

OTHER PUBLICATIONS

Sai Global (Downloaded from Internet May 16, 2013).*
Gruenwedel et al. (Separation Techniques vol. 4, 1987).*
Techstreet Store (downloaded from the internet Oct. 24, 2013).*
Gruenwedel et al. (Separation Techniques vol. 4, pp. 3, 1-16 and 44-48, 1987).*
M.T. Than (Basic Distillation Equipment and Operation, 2009, Downloaded from internet Feb. 14, 2014).*
M.T. Than (Basic Distillation Equipment and Operation, 2009).*
Pilling et al. (Choosing Trays and Packings for Distillation, 2009).*
European Search Report issued Mar. 23, 2011 in Patent Application No. 10191560.1 with English Translation of Category of Cited Documents.
International Search Report and Written Opinion issued Feb. 14, 2012 in PCT/EP2011/070159 with English Translation of Category of Cited Documents.
U.S. Appl. No. 13/299,039, filed Nov. 17, 2011, Bock, et al.
U.S. Appl. No. 13/298,851, filed Nov. 17, 2011, Bock, et al.

* cited by examiner

*Primary Examiner* — Yevegeny Valenrod
*Assistant Examiner* — Blaine G Doletski
(74) *Attorney, Agent, or Firm* — Oblon, McClelland, Maier & Neustadt, L.L.P.

(57) ABSTRACT

The invention relates to a method for purifying mixtures comprising 4,4'-methylenediphenyl diisocyanate, which comprises purifying by distillation a mixture I comprising 4,4'-methylenediphenyl diisocyanate having a hydrolyzable chlorine content as specified in ASTM D4663-10 of greater than 100 ppm by means of a column K1, wherein the gaseous stream comprising the mixture I is brought into contact in the column K1 with at least one liquid compound A which has the same or higher boiling point than 4,4'-methylenediphenyl diisocyanate and which has a hydrolyzable chlorine content as specified in ASTM D4663-10 of a maximum of 100 ppm, and wherein the gaseous stream O obtained at the top of the column comprises 4,4'-methylenediphenyl diisocyanate has a hydrolyzable chlorine content as specified in ASTM D4663-10 of a maximum of 100 ppm.

22 Claims, 1 Drawing Sheet

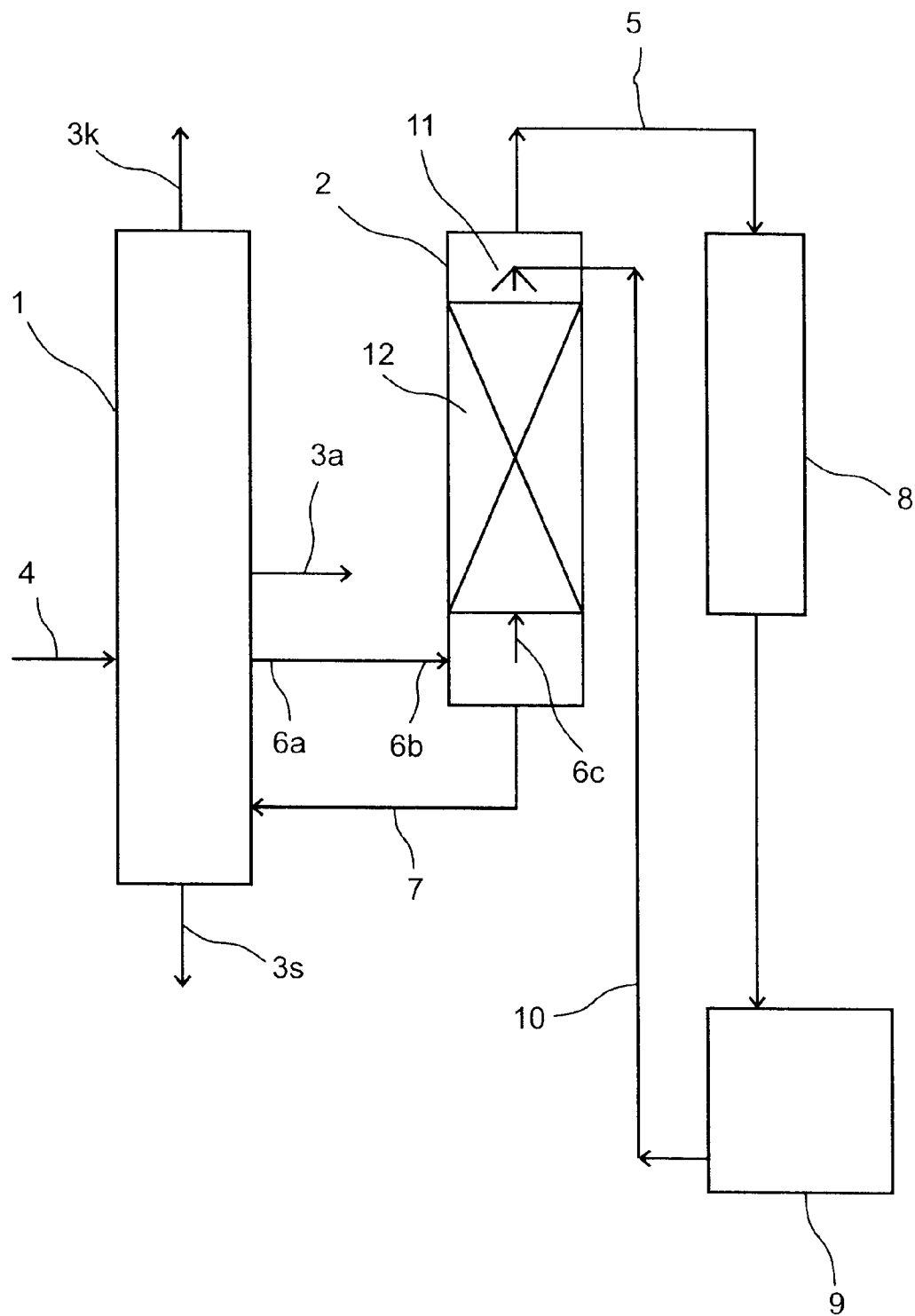

METHOD FOR PURIFYING MIXTURES COMPRISING 4,4'-METHYLENEDIPHENYL DIISOCYANATE

CROSS-REFERENCE TO RELATED APPLICATIONS

This application claims the benefit of priority under Section 119(e) of U.S. Provisional Application No. 61/414,446 filed on Nov. 17, 2010.

BACKGROUND OF THE INVENTION

The invention relates to a method for purifying mixtures comprising 4,4'-methylenediphenyl diisocyanate, which comprises purifying by distillation a mixture I comprising 4,4'-methylenediphenyl diisocyanate having a hydrolyzable chlorine content as specified in ASTM D4663-10 of greater than 100 ppm by means of a column K1, wherein the gaseous stream comprising the mixture I is brought into contact in the column K1 with at least one liquid compound A which has the same or higher boiling point than 4,4'-methylenediphenyl diisocyanate and which has a hydrolyzable chlorine content as specified in ASTM D4663-10 of a maximum of 100 ppm, and wherein the gaseous stream O obtained at the top of the column comprises 4,4'-methylenediphenyl diisocyanate has a hydrolyzable chlorine content as specified in ASTM D4663-10 of a maximum of 100 ppm.

Methylenediphenyl diisocyanate (MDI) is an important starting product for producing polyurethanes and related polymers that are used, for example, in foams and coatings. Pure 4,4'-MDI is a compound that is solid at room temperature and melts at 38° C.

The acid-catalyzed production of methylenediphenyl diisocyanate (MDI) starting from aniline and formaldehyde is known and leads first to a complex mixture of polyamines which is then reacted with phosgene. In this case, first a complex mixture of binuclear and polynuclear MDI is obtained which will hereinafter be called crude methylenediphenyl diisocyanate (crude MDI). Crude MDI comprises, in particular, the binuclear isomers 4,4'-MDI, 2,4'-MDI and to a lesser extent 2,2'-MDI (hereinafter termed together crude binuclear MDI) and also trinuclear or polynuclear MDI which will be termed hereinafter polymeric MDI (PMDI).

In known methods, crude MDI is separated into a PMDI-rich mixture and into crude binuclear MDI. Subsequently, customarily, 4,4'-MDI is separated off, firstly, and a 2,4'-MDI-rich mixture, secondly, is separated off from the crude binuclear MDI. Corresponding methods are described, for example, in the laid-open publications DE 1923214, DE 102005004170, DE 102005055189, CN 101003497 and DE 10333929.

For further use in said polymeric systems, in some cases a high purity, in particular a high isomeric purity, is necessary, since frequently only highly linear polymers of 4,4'-MDI have the desired end properties. In other cases, mixtures of the abovementioned isomers are used in the presence or absence of polynuclear MDI.

Before further processing, the methylenediphenyl diisocyanate products thus produced which are in liquid form must be stocked temporarily and/or stored.

Methylenediphenyl diisocyanate (MDI), in particular binuclear MDI, forms dimeric secondary products in the liquid phase after some time, i.e. during storage. In this case, in particular the formation of uretdiones by 4-membered ring formation owing to dimerization of two isocyanate groups and the formation of uretonimines by 4-membered ring formation from one carbodiimide group and one isocyanate group plays an important role. The formation of the 4-membered rings is in principle an equilibrium reaction which, by temperature elevation, can be shifted to the side of the isocyanates or carbodiimides. The formation of uretdiones also proceeds in the case of aromatic isocyanates uncatalyzed. A trimerization to give what are termed isocyanurates (1,3,5-triazine-2,4,6-triones) is likewise possible, but generally proceeds at a significant velocity only when a suitable catalyst is added.

The formation of the dimeric secondary products that are insoluble in the methylenediphenyl diisocyanate leads to disadvantageous hazes and sedimentations and results in quality decreases in the subsequent further processing, in particular owing to blockage of lines, apparatuses and machines.

A further problem is aromatic halogen compounds that are present in MDI. In the condensation of formaldehyde and aniline that is catalyzed by hydrochloric acid, chlorine-comprising byproducts form that are not at first separated off, but are reacted further with phosgene. In the reaction of the complex polyamine-comprising mixture with phosgene, further chlorine-comprising compounds form, in particular N,N-disubstituted (secondary) carbamoyl chlorides and chlorinated phenyl isocyanates.

Aromatic halogen compounds should be avoided, in particular, when, at elevated temperatures, they are chemically converted into compounds having readily hydrolyzable halogen. Hydrolyzable halogen compounds, in particular when they occur in variable concentrations, interfere with the reaction of isocyanates with polyols to form polyurethanes, since the reaction rate is effected by the halogen compounds. In addition, they cause a more rapid yellow discoloration of the isocyanates occurring first clear and colorless. From a multiplicity of such aromatic halogen compounds those which may be mentioned by way of example are: N,N-dimethylaniline hydrochloride, N-chloroformylaniline, N-methyl-N-chloroformylaniline and also compounds of the formulae

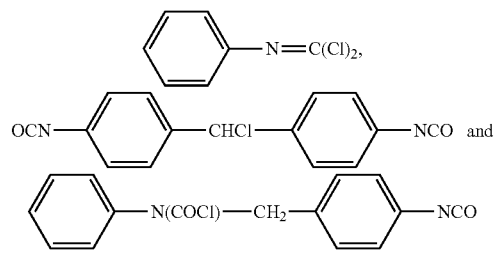

A method which reduces the content of aromatic halogen compounds in mixtures comprising 4,4'-MDI or provides such a mixture having a low content of aromatic halogen compounds is therefore desirable.

Methods for producing methylenediphenyl diisocyanate having a low content of chlorine compounds are known per se from the prior art.

DE-OS 2631168 describes the production of diisocyanates which can be adjusted with respect to their chlorine content. For this purpose a mixture of isomers comprising substantially 2,4'- and 4,4'-MDI is first freed in a distillation column from the majority of the impurities boiling higher than 4,4'-MDI and then the resultant distillate is freed by distillation from the impurities boiling more readily than 2,4'-MDI. The proposed technical solution, however, is very complex in terms of apparatus. The depletion in secondary carbamoyl chlorides in the resultant 4,4'-MDI is in addition frequently inadequate.

DE-OS 2933601 describes a method for producing polymeric MDI and monomeric MDI having a lower fraction of uretdiones and hydrolyzable chlorine compounds. In a first stage, binuclear MDI is separated off from PMDI (thin-film evaporator 175-210° C.). The distillate from the thin-film evaporator is condensed in the presence of an inert gas and then the MDI isomers are separated from one another by distillation. The resultant 4,4'-MDI, however, still comprises unwanted compounds that boil higher than 4,4'-MDI. In addition, the method does not always allow itself to be integrated in an economic manner in an overall process.

DD-P 288599 A5 describes a method for reducing the content of chlorine-comprising compounds in isocyanates by admixture with carbodiimides and subsequent stripping. The thermal dehalogenation, however, does not lead to complete breakdown of the halogen compounds. Thus the secondary carbamoyl chlorides may be incompletely removed. Owing to the high thermal stress of the resultant product, in addition, unwanted breakdown products form. The addition of carbodiimides, in addition to the stated reduction in chlorine, causes an increase in the molecular weight due to trimerization reactions.

Certain aromatic halogen compounds that are predominantly difficult to hydrolyze and have a higher boiling point than 4,4-MDI, however, may not be removed from 4,4'-MDI-comprising mixtures by methods of the prior art, or may not be removed to a sufficient extent. Furthermore, the methods known from the prior art may not always be integrated to a satisfactory extent into known methods for producing MDI.

It was therefore an object of the invention to find a method for purifying 4,4'-MDI-comprising mixtures which does not have the abovementioned disadvantages, or has them to a decreased extent.

It was an object of the present invention, in particular, to produce mixtures of MDI isomers, in particular mixtures of 2,4'- and 4,4'-MDI and also pure 4,4'-MDI having a lower content of uretdiones and uretonimines and also hydrolyzable chlorine compounds. The method should be able to be implemented with a low expenditure on apparatus and be mild toward MDI.

The object was, in particular, to provide a mixture comprising 4,4'-MDI, which mixture has a low content of hydrolyzable chlorine compounds. In particular, the content of chlorinated phenyl isocyanates and of chlorinated byproducts which pass into the phosgenation from byproducts of the aniline-formaldehyde condensation that are not separated off should be as low as possible.

The method should be able to be integrated with the lowest possible expenditure on resources into existing technologies for producing binuclear MDI.

BRIEF SUMMARY OF THE INVENTION

The objects describe above are satisfied by a method for purifying mixtures comprising 4,4'-methylenediphenyl diisocyanate, which comprises purifying by distillation a mixture I comprising 4,4'-methylenediphenyl diisocyanate having a hydrolyzable chlorine content as specified in ASTM 04663-10 of greater than 100 ppm by means of a column K1, wherein the gaseous stream comprising the mixture I is brought into contact in the column K1 with at least one liquid compound A which has the same or higher boiling point than 4,4'-methylenediphenyl diisocyanate and which has a hydrolyzable chlorine content as specified in ASTM 04663-10 of a maximum of 100 ppm, and wherein the gaseous stream o obtained at the top of the column comprises 4,4'-methylenediphenyl diisocyanate has a hydrolyzable chlorine content as specified in ASTM 04663-10 of a maximum of 100 ppm.

BRIEF DESCRIPTION OF THE DRAWING

FIG. 1 is a schematic of a preferred embodiment of the present invention.

DETAILED DESCRIPTION OF THE INVENTION

The abovementioned objects are achieved by the method according to the invention. Preferred embodiments may be found in the claims and the description hereinafter. Combinations of preferred embodiments do not depart from the scope of the present invention.

The method according to the invention for purifying mixtures comprising 4,4'-methylenediphenyl diisocyanate, which comprises purifying by distillation a mixture I comprising 4,4'-methylenediphenyl diisocyanate having a hydrolyzable chlorine content as specified in ASTM D4663-10 of greater than 100 ppm, preferably greater than 150 ppm, by means of a column K1, wherein the gaseous stream comprising the mixture I is brought into contact in the column K1 with at least one liquid compound A which has the same or higher boiling point than 4,4'-methylenediphenyl diisocyanate and which has a hydrolyzable chlorine content as specified in ASTM D4663-10 of a maximum of 100 ppm, preferably of a maximum of 50 ppm, and wherein the gaseous stream O obtained at the top of the column comprises 4,4'-methylenediphenyl diisocyanate has a hydrolyzable chlorine content as specified in ASTM D4663-10 of a maximum of 100 ppm, preferably of a maximum of 50 ppm.

The expression "purifying mixtures comprising 4,4'-methylenediphenyl diisocyanate" denotes the conversion of a first mixture comprising 4,4'-methylenediphenyl diisocyanate into a second mixture, the 4,4'-methylenediphenyl diisocyanate content (in % by weight) of which is higher than that of the first mixture. The purification by distillation comprises any single- or multistage purification which in at least one step comprises a distillation.

The expression "distillation" or "by distillation" denotes the purification of a mixture by means of a separation method by distillation. Separation methods by distillation are characterized in that the separation action is based on the differing composition of the boiling liquid and the gaseous vapor.

The content in ppm, in the context of the present invention, relates fundamentally to parts by weight based on the total weight of a mixture.

Aromatic halogen compounds are chemical compounds that comprise at least one aromatic ring and at least one halogen atom.

A column is a device for purification of a mixture by distillation. In the context of the present invention, a column is taken to mean a rectification column. Columns are known per se to those skilled in the art.

A column comprises a preferably longitudinal container having separation elements. Separation elements are internals which intensify the heat exchange and mass transfer.

The column comprises in addition a region below the lowermost separation element which can receive the condensate (the bottom phase) and a region above the uppermost separation element, the top. For vaporizing the mixture of matter that is to be separated, an evaporator can be arranged beneath the bottom phase of the rectification column. For condensation of the gaseous stream exiting at the top, a condenser can be connected downstream of the column top.

Depending on the type of the separation elements used, a distinction is made between tray columns, packed-bed columns and ordered-packing columns. By means of a feed which is frequently applied at the bottom of a column, the vaporized mixture of the substances that are to be separated is fed in. Toward the top, the lower-boiling component is enriched and can there be taken off, whereas the higher-boiling component is recirculated. In the bottom phase the higher-boiling component is enriched and can there be taken off.

A distinction is customarily made between three types of separation elements. In tray columns, sieve trays, bubble-cap trays or valve trays are installed, on which the liquid stands. By means of special slots or holes, the vapor is bubbled into the liquid and so a bubbling layer forms. On each of these trays, a new temperature-dependent equilibrium between the liquid phase and gas phase is established.

Packed-bed columns can be packed with different packing elements that cause good distribution of the liquid and vortexing of the gas flow. By means of the surface area enlargement, heat exchange and mass transfer are optimized and the separation capacity of the column thereby increased. Known examples are the Raschig ring (a hollow cylinder), Pall ring, Hiflow ring, Intalox saddle, Berl saddle and hedgehog packing. The packing elements can be introduced in an arranged manner into the column but also randomly (as a bed).

Ordered-packing columns having packings as separating bodies (packing elements) are a further development of the arranged packing bodies. They have a regularly shaped structure. As a result, it is possible in the case of ordered packings to reduce constrictions for the gas flow (with considerable effect on the pressure drop). There are various designs of ordered packings, e.g. woven fabric or metal sheet packings.

The hydrolyzable chlorine content is determined in the context of the present invention in principle as specified in ASTM D4663-10 and characterizes the content of aromatic chlorine compounds that are hydrolyzable under the conditions of ASTM D4663-10 (frequently termed "DHC" or difficultly hydrolyzable chlorine). Therefrom, a distinction may be made between the total chlorine content as specified in ASTM D 4661-09 which also determines ring-substituted chlorine compounds such as monochlorobenzene, and what is termed the content of easily hydrolyzable chlorine (EHC) as specified in ASTM D 5629-05 which characterizes the acidity in the form of HCl.

Preferred embodiments of the method according to the invention are described hereinafter.

The production of suitable starting mixtures comprising 4,4'-methylenediphenyl diisocyanate is known to those skilled in the art.

The method can be used in principle with any mixture comprising 4,4'-methylenediphenyl diisocyanate, provided that the mixture is susceptible to processing by distillation. The content of the compound 4,4'-methylenediphenyl diisocyanate in the mixture I used is preferably at least 95% by weight, in particular at least 98% by weight. The method according to the invention, however, can in principle also be employed for mixtures of 2,4'-MDI and 4,4'-MDI, if, in the separation of isomers, 4,4'-MDI is not obtained separately.

It is known to those skilled in the art how the abovementioned mixtures comprising 4,4'-methylenediphenyl diisocyanate can be obtained. Firstly, in a first step aniline and formaldehyde are condensed, and then the resultant polyamine mixture (polyaminopolyphenylpolymethanes) is phosgenated.

The condensation of aniline and formaldehyde and also the phosgenation of the polyaminopolyphenylpolymethanes is well known from the prior art. After the phosgenation of polyaminopolyphenylpolymethanes, first phosgene is completely eliminated. Then, the polynuclear homologs of methylenediphenyl diisocyanate (PMDI) are separated off, wherein what is termed crude binuclear MDI is obtained. Crude binuclear methylenediphenyl diisocyanate (MDI) is known to those skilled in the art as a mixture that, in addition to 4,4'-methylenediphenyl diisocyanate, additionally comprises at least one of the isomers 2,2'- and 2,4'-methylenediphenyl diisocyanate. The 4,4'-methylenediphenyl diisocyanate content in crude binuclear methylenediphenyl diisocyanate is customarily less than 80% by weight, in particular less than 60% by weight.

From crude binuclear methylenediphenyl diisocyanate, pure 4,4'-methylenediphenyl diisocyanate is then separated off. For the separation, various methods based on a distillation or crystallization or a combination of distillation and crystallization are known from the prior art.

The method according to the invention can advantageously be integrated into known methods for producing mixtures comprising 4,4'-MDI, in particular by combining it with a distillation for separating off said isomeric (binuclear) methylenediphenyl diisocyanates. This will be discussed hereinbelow.

According to the present invention, the gaseous stream comprising the mixture I is brought into contact in the column K1 with at least one liquid compound A which has the same or a higher boiling point than 4,4'-methylenediphenyl diisocyanate and which has a hydrolyzable chlorine content as specified in ASTM D4663-10 of a maximum of 100 ppm, preferably a maximum of 50 ppm, particularly preferably a maximum of 30 ppm, in particular a maximum of 20 ppm, very particularly preferably a maximum of 10 ppm.

In principle, compounds come into consideration as liquid compounds A which are either inert to 4,4'-methylenediphenyl diisocyanate or are 4,4'-methylenediphenyl diisocyanate itself.

Suitable inert compounds A are, in particular, dibenzyl ether, terphenyl, higher esters of phthalic acid and naphthalene derivatives. Of course, mixtures of the abovementioned inert compounds also come into consideration.

However, particularly preferably, the compound A is 4,4'-methylenediphenyl diisocyanate. Particularly preferably, as compound A, in this case 4,4'-methylenediphenyl diisocyanate is used having a purity of at least 97% by weight, particularly preferably at least 98% by weight, in particular at least 98.5% by weight. However, in principle, a mixture of 4,4'-methylenediphenyl diisocyanate of said purity having at least one of the abovementioned inert compounds can also be used. In each case, the hydrolyzable chlorine content as specified in ASTM D4663-10 in compound A is a maximum of 100 ppm.

Very particularly preferably, the compound A is 4,4'-methylenediphenyl diisocyanate that has already passed through the purification by distillation according to the invention. 4,4'-Methylenediphenyl diisocyanate which has already passed through the purification by distillation according to the invention and must be stored in a suitable manner, wherein the dimeric secondary products mentioned at the outset form, is thereby recirculated in proportion back to the process. At the same time two advantages can thereby be achieved: firstly, according to the invention 4,4'-MDI which is low in aromatic halogen compounds is made accessible and secondly, stored 4,4-MDI which, as a consequence of the storage, was partially broken down to secondary products, is recycled and passes in high-purity form to the storage, whereby the quality of the stored 4,4'-MDI overall can be optimized. In this case the storage-recycle ratio (amount of recirculated 4,4'-MDI in relation to the amount of 4,4'-MDI newly fed to the storage (additionally obtained)) is preferably 0.05 to 0.4, in particular 0.1 to 0.3.

Very particularly preferably, the compound A is 4,4'-methylenediphenyl diisocyanate which is recirculated from a device for storing 4,4'-methylenediphenyl diisocyanate. A device for storage in this case is any device which is provided for the temporary reception of the substance or mixture of substances that is to be stored, for example a container, for example a storage tank.

The liquid compound A is added above the uppermost separation element of the column K1. In a preferred embodiment, the column K1 is an ordered-packing column. The specific surface area of the ordered packing is preferably from 100 to 1000 $m^2/m^3$, particularly preferably from 150 to 800 $m^2/m^3$, in particular from 200 to 750 $m^2/m^3$, very particularly preferably from 250 to 600 $m^2/m^3$.

In principle, preference is given to those ordered packings which cause a low pressure drop. Suitable ordered packings are, in particular, woven fabric packings, sheet metal packings and structured packings. Woven fabric packings are particularly preferred.

The liquid compound A is added, preferably, above the highest packing element of the column K1.

According to the present invention, the gaseous stream comprising the mixture I in the column K1 is brought into contact with at least one liquid compound A. In principle, a plurality of contacting methods come into consideration. Preference in this case is given to those methods which lead to an intense contact between the gas stream and the liquid compound A. For this, the liquid A must be distributed in a suitable manner. Corresponding methods are known per se to those skilled in the art.

The effectiveness of the contacting is dependent, in particular, on a uniform, surface-covering liquid application. Liquid distributors ensure a substantially homogeneous liquid distribution over the column cross section and are known to those skilled in the art.

A predistribution of the liquid can be effected by one or more feed tubes or distributor channels having a plurality of outlet openings which are situated on the lower side.

An important design variable is the number of delivery points based on the column cross section (=dripping point density). The following types of liquid distributors come into consideration: distributor trays, channel distributors, tube distributors and nozzle distributors. The following principles of liquid distribution come into consideration: damming height distribution over boreholes in the tray of distributors or laterally bored delivery tubes, overflow distribution, e.g. over side slots or overflow spouts and nozzles.

Suitable liquid distributors are, in particular, box channel distributors. It is advantageous if the contacting proceeds in countercurrent flow to the gaseous stream I. A particularly low content of aromatic halogen compounds in the resultant mixture results thereby.

The feed of the mixture I into the column K1 can proceed in principle in various ways, more precisely in liquid form or in gaseous form. In the case of a feed in liquid form, the use of a suitable evaporator is advantageous. Preferably, the mixture I is fed into the column K1 in gaseous form.

The absolute pressure at the top of the column K1 is preferably a maximum of 50 mbar, particularly preferably 1 to 30 mbar, in particular 2 to 20 mbar. The pressure difference between top and bottom phase (pressure drop) of the column K1 is preferably 0.5 to 30 mbar, preferably from 0.5 to 20 mbar, particularly preferably 1 to 10 mbar, in particular 2 to 5 mbar. A low pressure drop causes a lower thermal stress of the product owing to lower bottom phase temperatures.

The temperature in the bottom phase of the column K1 is 140 to 270° C., preferably 150° C. to 240° C., particularly preferably 170 to 230° C., in particular 190 to 230° C., very particularly preferably 200 to 225° C. The thermal stress is thereby minimized for a given efficiency of purification.

The reflux ratio, defined here as the ratio of scrubbing liquid to vapors S:V [w/w] is S:V=0.01 to 2.0, preferably S:V=0.05 to 0.5, particularly preferably S:V=0.1 to 0.3.

The column K1 can be fabricated from various materials, provided that the materials used are inert to the mixtures used at a given temperature. Suitable materials are, in particular, austenitic stainless steels such as 1.4541 or 1.4571. Higher-alloyed materials such as the ferritic/austenitic 1.4462 are also suitable. Preferably, the material 1.4541 is used.

At the top of the column K1, a stream O is obtained which comprises the purified mixture comprising 4,4'-methylenediphenyl diisocyanate and has a hydrolyzable chlorine content as specified in ASTM D4663-10 of a maximum of 100 ppm, preferably a maximum of 50 ppm. The stream O is then subjected to cooling, by cooling the stream O to a temperature of preferably 10 to 100° C., in particular 20 to 80° C., in particular 20 to 60° C.

The stream O is preferably cooled in a maximum of 5 seconds from the temperature at the top of the column K1 to a temperature in the range from 20° C. to 60° C., preferably from 30° C. to 50° C. By means of the rapid cooling, the formation of secondary products, in particular the formation of dimeric secondary products, is further reduced. Such secondary products are unwanted and reduce the storability of the product.

Corresponding methods for rapid cooling of MDI-comprising initially gaseous streams ("quenching") are known per se to those skilled in the art. In principle, direct quenching and indirect quenching come into consideration. In the case of direct quenching, the stream O is introduced into a liquid compound A* which has a correspondingly low temperature. In a preferred first embodiment, the compound A* is an isocyanate, preferably MDI, in particular binuclear MDI. Particularly preferably, the compound A* is 4,4'-MDI, in particular that which has already passed through the method according to the invention. In a second preferred embodiment, the compound A* is an inert solvent which must then be removed. Corresponding methods are known to those skilled in the art.

The feed of the gaseous stream O into the device for direct or indirect quenching is adjusted by a person skilled in the art in such a manner that the cooling according to the invention proceeds in a maximum of 5 seconds, preferably in a maximum of 4 seconds, in particular in a maximum of 3 seconds.

In the case of indirect quenching, the quenching proceeds in a heat exchanger in which a liquid taking up the heat is preferably conducted in countercurrent flow to the initially gaseous stream O without coming into direct contact with the stream O. By means of the cooling, the stream O condenses. The heat exchanger is therefore also termed a condenser. Suitable heat exchangers are likewise known to those skilled in the art. Preferred heat exchangers are, in particular, upright condensers, tube-bundle condensers, upright tube-bundle condensers and upright plate condensers. The expression upright characterizes the vertical arrangement. Indirect quenching is particularly preferred in the context of the present invention.

In a particularly preferred embodiment, an inert gaseous medium, in particular nitrogen, is added to the gaseous stream O that is to be cooled according to the invention before quenching.

Preferably, the inert gaseous medium is added in the bottom phase of a condenser (heat exchanger) in which the quenching is carried out. The addition proceeds preferably in counter-current flow through the condenser.

Alternatively, the addition proceeds before the feed into the device for quenching the gaseous stream O by means of a suitable mixing device, or in the region of the feed of the gaseous stream O into the device for quenching.

By means of the mixture with the inert medium, the content of unwanted low boilers in the method according to the invention is further decreased.

By means of the combination of the measures of the purification by means of distillation according to the invention, firstly, and the quenching according to the invention, secondly, mixtures comprising 4,4'-MDI are obtained that have a high purity not only with respect to hydrolyzable chlorine compounds but also with respect to dimers.

According to the invention the mixture obtained that comprises 4,4'-methylenediphenyl diisocyanate still comprises a maximum of 100 ppm of the hydrolyzable chlorine as specified in ASTM D4663-10. Preferably, the hydrolyzable chlorine content as specified in ASTM D4663-10 in the stream O is a maximum of 80 ppm, in particular a maximum of 50 ppm, particularly preferably a maximum of 30 ppm, in particular a maximum of 20 ppm, very particularly preferably a maximum of 10 ppm.

Preferably, the mixture obtained comprising 4,4'-methylenediphenyl diisocyanate has a total chlorine content as specified in ASTM D4661-09 of a maximum of 200 ppm. Particularly preferably, the total chlorine content as specified in ASTM D4661-09 in the stream O is a maximum of 150 ppm, in particular a maximum of 100 ppm, particularly preferably a maximum of 70 ppm, in particular a maximum of 40 ppm, very particularly preferably a maximum of 20 ppm. The total chlorine content as specified in ASTM D4661-09 differs from the hydrolyzable chlorine content as specified in ASTM D4663-10 essentially due to taking into account ring-chlorinated aromatic chlorine compounds.

Preferably, the mixture obtained that comprises 4,4'-methylenediphenyl diisocyanate has an acidity as specified in ASTM D5629-05 of a maximum of 40 ppm. Particularly preferably, the acidity as specified in ASTM D5629-05 is a maximum of 30 ppm, in particular a maximum of 20 ppm, very particularly preferably a maximum of 10 ppm, in particular a maximum of 5 ppm.

The hydrolyzable chlorine content of the mixture I that is to be purified and comprises 4,4'-methylenediphenyl diisocyanate as specified in ASTM D4663-10 is, according to the invention, at least 100 ppm, preferably at least 120 ppm, in particular at least 150 ppm, particularly preferably at least 200 ppm, in particular at least 250 ppm.

It is obvious to those skilled in the art that by means of the method according to the invention, the corresponding bromine compound content is also reduced, even though the success is characterized via the chlorine compounds.

In principle, as aromatic chlorine compounds, a multiplicity of compounds come into consideration which are formed from unseparated byproducts of the aniline/formaldehyde condensation in secondary processes, or in other ways during the phosgenation.

The abovementioned reduction in total chlorine content as specified in ASTM D4661-09 relates in particular to halogenated phenyl isocyanates of the general formula I. Halogenated phenyl isocyanates are taken to mean a mono- or di-ring-chlorinated or brominated phenyl isocyanate, in particular a singly ring-chlorinated phenyl isocyanate. Preferably, the content of halogenated phenyl isocyanates in the stream O should be a maximum of 25 ppm, particularly preferably a maximum of 15 ppm, in particular a maximum of 10 ppm:

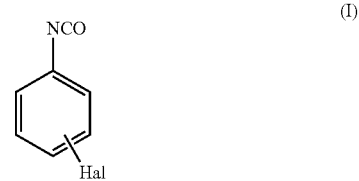

Further aromatic halogen compounds which are unwanted in relatively large amounts in the purified 4,4'-methylenediphenyl diisocyanate are N,N-disubstituted (secondary) carbamoyl chlorides of the general formula II, the content of which in the stream O should preferably be a maximum of 25 ppm, particularly preferably a maximum of 15 ppm, in particular a maximum of 10 ppm:

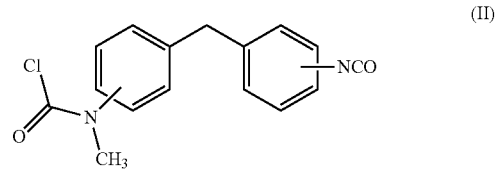

These include, in particular, the following compounds which are formed in the phosgenation of crude MDA: 4-isocyanato-4'-N-methylcarbamoyl chloridodiphenylmethane, 2-isocyanato-4'-N-methylcarbamoyl chloridodiphenylmethane and 2-isocyanato-2'-N-methylcarbamoyl chloridodiphenylmethane.

N-Phenyl-N-isocyanatobenzylcarbamoyl chlorides of the general formula III, in particular N-phenyl,N-4-isocyanatobenzylcarbamoyl chloride and N-phenyl,N-2-isocyanatobenzylcarbamoyl chloride, which are formed in phosgenation from non-rearranged aminobenzylanilines, likewise come into the class of secondary carbamoyl chlorides:

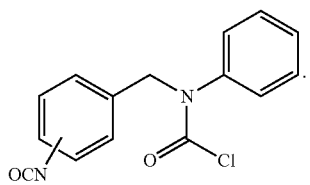

(III)

Further aromatic halogen compounds which are unwanted in relatively large amounts in the purified 4,4'-methylenediphenyl diisocyanate are isocyanatobenzyl halides of the general formula IV, in particular 4-isocyanatobenzyl chloride and 2-isocyanatobenzyl chloride, the content of which in stream O should preferably be a maximum of 25 ppm, particularly preferably a maximum of 15 ppm, in particular a maximum of 10 ppm:

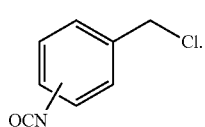

(IV)

The content of the abovementioned compounds of the general formulae I, II, III and IV is decreased by the method according to the invention. Preferably, the content of aromatic halogen compounds of the general formulae I, II, III and IV in the stream O is overall at least 10 ppm, preferably at least 50 ppm, particularly preferably at least 100 ppm, in particular at least 150 ppm, lower than in the mixture I. Preferably, the content of aromatic halogen compounds of the general formulae I, II, III and IV in the stream O is overall a maximum of 40 ppm, particularly preferably a maximum of 30 ppm, very particularly preferably a maximum of 20 ppm, in particular a maximum of 10 ppm.

As already stated at the outset, the method according to the invention can advantageously be integrated into known methods for producing mixtures comprising 4,4'-methylenediphenyl diisocyanate, wherein the linkage to a separation by distillation of the isomers of the binuclear methylenediphenyl diisocyanate is particularly preferred. Very particular preference is given to the combination with a separation by distillation of 4,4'-methylenediphenyl diisocyanate firstly and a mixture comprising 2,4'- and 4,4'-methylenediphenyl diisocyanate, secondly.

One example of a separation by distillation of 4,4'-diisocyanatodiphenylmethane which can advantageously be combined with the method according to the invention is described in DE-OS 2 631 168, the contents of which are hereby incorporated in the present application in entirety. DE-OS 2 631 168 describes the multistage workup of a mixture of polyisocyanatopolyphenyl-polymethanes to give diisocyanatodiphenylmethane isomers. After separation by distillation of the higher-functional isocyanates, the first distillation stream occurring at this stage, comprising substantially 2,2'-MDI, 2,4'-MDI and 4,4'-MDI, is fed to a first column and separated into a further distillation stream and a bottom-phase stream. The bottom-phase stream can be up to 10% by weight of the first distillation stream. The second distillation stream is fractionated in a second column into an overhead stream which comprises volatile impurities, 2,2'-diisocyanatodiphenylmethane and 2,4'-MDI, and a bottom-phase stream which comprises the predominant fractions of 2,4'-MDI and 4,4'-diisocyanatodiphenylmethane. This bottom-phase stream is separated in a third column into 4,4'-MDI and a distillate fraction enriched with 2,4'-MDI. In the last distillation stage, 4,4'-MDI distils having a content of less than 2% by weight of 2,4'-MDI.

Further methods for obtaining by distillation 4,4'-MDI or mixtures of 4,4'- and 2,4'-MDI are described, e.g., in DE-A-2 933 601 and DE-A-3 145 010. In DE-A-3 145 010 it is proposed that, from the mixture of isomers of the diisocyanatodiphenylmethanes, first, as overhead product, 2,2'- and 2,4'-diisocyanatodiphenylmethane is taken off and as bottom-phase product, 4,4'-MDI substantially freed from isomers is obtained. This bottom-phase product must then be freed in a final distillation from polymerization products that have formed during the thermal stress, whereas the overhead product can be fed according to the present invention to the further workup by distillation.

In a preferred embodiment, the mixture I which is fed to the column K1 according to the invention accordingly originates from a second column K2, in which crude binuclear methylenediphenyl diisocyanate is completely or partly separated into its isomers, preferably in which 4,4'-MDI is completely or predominantly separated off from the isomers 2,4'-MDI and/or 2,2'-MDI, wherein the content of 4,4'-MDI of the mixture that is separated off is preferably at least 90% by weight 4,4'-MDI based on the total weight of the mixture, particularly preferably at least 95% by weight, in particular at least 98% by weight.

Column K2 preferably comprises separation elements, wherein ordered packings are particularly suitable. Those which are usable, however, are in principle also packed beds or trays. The column K2 is preferably a side stream column. A side stream column is taken to mean a column that has at least one bottom-phase takeoff, at least one side stream takeoff, and at least one overhead takeoff.

Depending on mixture composition, the overhead temperature of the column K2 is preferably 165 to 200° C. The bottom-phase pressure is preferably 11 to 20 mbar at preferred temperatures of 210 to 225° C. The column K2 operates preferably at a bottom-phase pressure of 0.1 to 50 mbar, preferably from 1 to 30 mbar, particularly preferably 2 to 15 mbar, and at a bottom-phase temperature of 150 to 250° C., particularly preferably from 180 to 240° C., in particular from 200 to 225° C. A high separation efficiency is thereby achieved with simultaneously low thermal stress.

In the distillation of the mixture of isomeric methylenediphenyl diisocyanates in the column K2, as side stream, 4,4'-methylenediphenyl diisocyanate is preferably taken off at an isomeric purity, i.e. a purity based on the three isomers 2,2'-MDI, 2,4'-MDI and 4,4'-MDI, of at least 97% by weight (hereinafter first side stream or first side stream takeoff).

Furthermore, in the distillation of the mixture of isomeric methylenediphenyl diisocyanates in the column K2, as second side stream takeoff which is situated above the first side stream takeoff, or as overhead stream, a mixture of 2,4'-diisocyanatodiphenylmethane and 4,4'-diisocyanatodiphenylmethane having a weight ratio of 85:15 to 15:85 is obtained. The embodiment having a second side stream takeoff above the first side stream takeoff is preferred, since a high purity of the desired binuclear isomers is thereby obtained. The overhead stream of the column K2 comprises, in addition, the low-boiler components supplied with the feed such as, e.g., monochlorobenzene.

The stream which is obtained at the second side stream takeoff or at the top of the column K2 preferably has a content of 2,4'-MDI of 20 to 95% by weight, and a 4,4'-MDI content of 5 to 80% by weight, in each case based on the total weight of the binuclear isomers of methylenediphenyl diisocyanate, which gives 100% by weight.

The column reflux ratio (ratio of returning material stream to material stream taken off) at the top of the column K2 is adjusted in particular in the range from 5 to 250, but is particularly preferably in the range from 10 to 120, wherein the distillate stream is 1 to 5% by weight based on the feed stream. The bottom-phase stream is 60 to 90% by weight, preferably 75 to 85% by weight of the feed stream.

In a first preferred embodiment, the column K2 is a dividing wall column. The structure of such a column K2 is known per se to those skilled in the art and is described, for example, in EP 1475367 A1. The dividing wall column is preferably operated under the conditions described above for the column K2. The mixture of isomeric binuclear methylenediphenyl diisocyanates is fed to the dividing wall column, preferably at the side in the region of the dividing wall. The region of the dividing wall is situated in the central region of the column K2. The length of the dividing wall is selected in dependence on the process conditions and on the properties of the mass transfer elements used. The dividing wall divides the column into a prefractionation zone and a main fractionation zone. As dividing elements, ordered packings are particularly suitable. However, packed beds or trays are also usable in principle.

Alternatively, separation by distillation of the binuclear MDI isomers can also be designed to be in two stages, wherein a first distillation stage is carried out in a distillation column without a dividing wall, and a second stage with a dividing wall column, or wherein two dividing wall columns are used. Corresponding methods are discussed in EP 1475367 A1 in paragraphs [0024] to [0031].

In a second preferred embodiment, the column K2 is a side stream column without a dividing wall. The preferred parameters of the side stream column have already been described above. In this case by means of the overhead takeoff, preferably 2,2'-MDI and low boilers are separated off and by means of the bottom-phase takeoff, preferably 4,4'-MDI and high boilers are taken off, wherein the stream from the bottom-phase takeoff and overhead takeoff can be used again in step (b) of the method according to the invention. Preferably, as described above, 4,4'-MDI is taken off from the side stream column in a first side stream takeoff at a purity of at least 97% by weight, based on the total weight of the material stream and also, above the first side stream takeoff, the above described mixture of 4,4'-MDI and 2,4'-MDI, in a second side stream takeoff.

The mixture I is preferably taken off from the column K2 as a side stream and fed in the gaseous form to the column K1. The mixture I is 4,4'-MDI having preferably at least 98% by weight, particularly preferably 98.5 to 99.0% by weight, purity, based on the total weight of the mixture I.

Preferably, the gaseous stream comprising the mixture I is contacted in the column K1 with at least one liquid compound A which according to the invention has the same or higher boiling point than 4,4'-methylenediphenyl diisocyanate and which according to the invention has a hydrolyzable chlorine content as specified in ASTM D4663-10 of a maximum of 1000 ppm.

In a preferred embodiment, the product obtained in the bottom phase of the column K1 is recirculated to the second column K2. Firstly, the formation of waste products can thereby be avoided, and so the yield of the overall method is optimized. Secondly, it is ensured that at the same time particularly pure 4,4'-MDI is obtained.

The stream which is obtained at the top of the column K2 preferably has a 2,4'-MDI content of 20 to 95% by weight and a 4,4'-MDI content of 5 to 80% by weight, in each case based on the total weight of the binuclear isomers of methylenediphenyl diisocyanate, which gives 100% by weight. In addition, the overhead stream of the column K2 comprises the low-boiler components such as, e.g., chlorobenzene, that are supplied with the feed.

The mixtures produced according to the invention of diphenylmethane diisocyanate isomers, in particular of 2,4'- and 4,4'-diphenylmethane diisocyanates, are suitable preferably for producing polyurethane adhesives and coatings. Pure 4,4'-diphenylmethane diisocyanate is preferably used for producing polyurethane elastomers, polyurethane filaments and polyurethane bristles. Owing to the low content of hydrolyzable chlorine compounds, the polyurethanes are relatively stable against yellow discoloration under the effect of air and light.

It was a further object to stabilize the reactivity of the MDI. In the course of operation, it was found that reactivity variations in the MDI are reduced by building hot isocyanate lines with a temperature of >120° between plant parts made from comparatively corrosion-resistant materials (nickel-base alloys). This applies particularly to lines having a temperature between 180° C. and 220° C.

"Between plant parts" means, for example, transport lines between two adjacent plant sections, product transport between two columns, or the transport from the column outlet to the product cooler into the product tank. In these lines, the isocyanate content is more than 20 w % measured to DIN ISO 14896:2009.

Suitable materials for this purpose are Hastelloy or Inconel alloys. The nickel content of these alloys is at least 50 w %. Suitable materials for these lines are thus, for example, Alloy 200 (2.4066), Alloy 400 (2.4360), Alloy C-276 (2.4819), Alloy C-22 (2.4602), Alloy 59 (2.4605), Hastelloy C-4 (2.4610), Hastelloy C-22 (2.4602), and all standard Hastelloy subgroups.

A preferred embodiment of the present invention is shown schematically in FIG. 1. FIG. 1 here serves to illustrate this preferred embodiment of the present invention and is not to be understood as restricting. Individual elements of the preferred embodiment described hereinafter can advantageously be combined with above-described embodiments.

1—column K2
2—column K1
3a—upper side stream takeoff of column K2
3k—overhead stream from column K2
3s—bottom-phase stream from column K2
4—stream of binuclear MDI isomers (feed to column K2)
5—overhead stream O of column K1
6a—lower side stream takeoff of column K2
6b—stream of mixture I
6c—vapor of mixture I
7—bottom-phase stream from column K1
8—condenser
9—storage tank for liquid 4,4'-MDI
10—recirculation from storage tank
11—liquid distributor
12—ordered packing elements

DESCRIPTION OF THE PREFERRED EMBODIMENT ACCORDING TO FIG. 1

A stream (4) comprising a mixture of binuclear isomers of MDI is fed to the column K2 (1). At the bottom phase of the column K2 (1), the bottom-phase stream (3s) is obtained, and at the top, the overhead stream (3k). From a first side stream takeoff (6a) a stream (6b) is taken off that preferably comprises 98% by weight 4,4'-MDI and also, above the first side stream, a stream (3a) which comprises 4,4'-MDI and 2,4'-MDI. The stream (6b) forms the stream I which is fed in the gaseous state to the column K1 (2) and, as vapor, comprising the mixture I (6c) passes through the ordered packing elements (12) of the column K1 (2). In countercurrent flow to the direction of the stream 6c there flows 4,4'-MDI which is taken off from a storage tank (9) for liquid 4,4'-MDI and is fed via a recirculation (10) at the top of column K1 to a liquid distributor (11). The liquid distributor (11) provides a high contact area between the ascending gaseous stream 6c and the liquid stream of 4,4'-MDI moving in the opposite direction. At the bottom phase of the column K1 (2), the stream (7) is obtained which is recirculated to the column K2 (1). At the top of the column K1, the overhead stream O (5) is obtained which comprises the purified 4,4'-MDI. The gaseous stream (5) is fed to a condenser (8) in which the stream (5) is condensed. The high-purity liquid 4,4'-MDI thus obtained is then fed through a storage tank (9).

Example 1

According to the Invention

An apparatus was used as is shown schematically in FIG. 1. The isocyanate lines to column K2 (stream 4), and streams stream 3s, 7, were manufactured from Hastelloy-C4.

2.0 kg/h of crude MDI comprising 50.2% by weight 4,4'-MDI, 6.8% by weight 2,4'-MDI, 21.2% by weight 3-ring MDI were vaporized at a pressure of 5 mbar in a falling-film evaporator made of the material 1.4571.

After the condensation, a distillate comprising 85.1% by weight 4,4'-MDI, 12.6% by weight 2,4'-MDI, 2.3% by weight 3-ring MDI was obtained. The mass flow rate of the distillate deposited in the condenser was 0.690 kg/h.

The distillate was fed in liquid form to a side stream takeoff column K2. The column K2 and the bottom-phase evaporator comprised the material 1.4571. The column was equipped with structured packings which have a low pressure drop. The top pressure of the column was 5 mbar.

The column K2 comprised an enrichment part and a stripping part. In the stripping part of the column K2, the stream I was taken off in the gaseous state by means of a first side stream takeoff (6a) below an ordered packing element and fed to the column K1 (stream of mixture I). The bottom-phase outflow of column K1 (7) was fed to the column K2 below the feed to the column K2. Above the feed, a liquid fraction was taken off at an upper side stream takeoff (3a).

Stream I (6b) comprised 98.7% by weight 4,4'-MDI and 1.3% by weight 2,4'-MDI. The content of 3-ring compound was 530 ppm. The mass flow rate (6) was 0.79 kg/h. At the stream (3k), a mixture of 47% by weight 4,4'-MDI and 53% by weight 2,4'-MDI was taken off. The mass flow rate was 0.14 kg/h.

Purification side stream (6): the gaseous side stream (vapor of mixture I, 6c) was fed to the column K1 (2). The column K1 made of the material 1.4571 was equipped with a low-pressure drop ordered packing (structured) having a specific surface area of 500 m$^2$/m$^3$. The top pressure of the column was 15 mbar.

Feed of the liquid compound A: at the top of the column K1, a stream of the compound A comprising 98.5% by weight 4,4'-MDI and 1.5% by weight 2,4'-MDI in liquid form was added above the uppermost ordered packing element and distributed by means of a box channel liquid distributor (11). The mass flow rate of the compound A was 0.17 kg/h. The liquid A comprised 4,4'-MDI from a storage tank (9) that had been stored at 42° C. and in which storage tank high-purity 4,4'-MDI was taken up that had already passed through the method. The dimer content of compound A was 0.13% by weight. The weight ratio of product (10) recirculated to column K1 to the product fed to the storage tank (9) was continuously 0.26 g/g.

At the top of the column K1, a gaseous stream O (5) was obtained as product, which stream O comprised 98.5% by weight 4,4'-MDI and 1.5% by weight 2,4'-MDI. The mass flow rate here was 0.65 kg/h. The stream O (5) was cooled to 42° C. within 5 s in a condenser (8) and fed to the storage tank (9).

In the gaseous stream O, the hydrolyzable chlorine content as specified in ASTM D4663-10 was in the range according to the invention and was able to be significantly reduced compared with the content in stream I.

At the same time, a mixture having a low total chlorine content as specified in ASTM D4661-09 and having a low acidity as specified in ASTM D5629-05 was obtained.

Example 2

Not According to the Invention

The procedure was as in example 1, except that the mass flow rate of component A at the top of column K1 was reduced to 0 kg/h. Analogously to example 1, GC analyses were conducted on abovementioned samples. N,N-disubstituted carbamoyl chlorides of the formula II were determined at 0.00047 area %. The content of ring-chlorinated MDI was 0.024 area %.

The invention claimed is:

1. A method for purifying 4,4'-methylene diphenyl diisocyanate, the method comprising purifying a mixture by distillation through a distillation column, such that a first gaseous stream comprising the mixture contacts at least one liquid compound within the distillation column, to obtain a second gaseous stream at a top of the distillation column, which is removed to obtain purified 4,4'-methylene diphenyl diisocyanate, wherein:
the mixture comprises 4,4'-methylenediphenyl diisocyanate having a hydrolyzable chlorine content of greater than 100 ppm as determined by ASTM D4663-10;
the second gaseous stream comprises the purified 4,4'-methylenediphenyl diisocyanate having a maximum hydrolyzable chlorine content of 100 ppm as determined by ASTM D4663-10;
wherein said distillation column comprises ordered packing elements and wherein said first gaseous stream is fed into said distillation column at a point below said ordered packing elements; and
said first gaseous stream is taken off as a side stream from a first column, and a product obtained from a bottom phase of said distillation column is recirculated to said first column.

2. The method according to claim 1, wherein the at least one liquid compound is added above an uppermost separation element of the distillation column, such that the at least one liquid compound is predistributed to a plurality of delivery points to the distillation column.

3. The method according to claim 1, wherein the at least one liquid compound is added to the distillation column through a liquid distributor.

4. The method according to claim 1, wherein the mixture is fed into the distillation column in gaseous form.

5. The method according to claim 1, wherein the second gaseous stream is cooled in at most 5 seconds to a temperature of 20° C. to 60° C. after its removal from the distillation column.

6. The method according to claim 1, wherein the hydrolyzable chlorine content of the second gaseous stream and the at least one liquid compound is, in each case, a maximum of 50 ppm as determined by ASTM D4663-10.

7. The method according to claim 1, wherein a maximum total chlorine content in the second gaseous stream is 100 ppm as determined by ASTM D4661-09.

8. The method according to claim 1, wherein a maximum content of halogenated phenyl isocyanates in the second gaseous stream is 25 ppm.

9. The method according to claim 1, wherein a maximum content of N,N-disubstituted carbamoyl chlorides in the second gaseous stream is 25 ppm.

10. The method according to claim 1, wherein the hydrolyzable chlorine content in the second stream is at least 10 ppm less than in the mixture as determined by ASTM D4663-10.

11. The method according to claim 1, wherein the mixture, before feeding into the distillation column, is taken off from a second said first column in which crude binuclear methylenediphenyl diisocyanate is completely or partially separated into its isomers.

12. The method according to claim 1, wherein a pressure difference between the first gaseous stream and the second gaseous stream, in the distillation column, is 0.5 to 30 mbar.

13. The method according to claim 1, wherein the distillation column is an ordered-packing column having a specific surface area of 100 to 1000 $m^2/m^3$.

14. The method according to claim 1, wherein the distillation occurs such that a reflux ratio in the distillation column is ranges from 0.01 to 2.0.

15. The method according to claim 1, wherein said at least one liquid compound comprises at least 98 wt. % 4,4'-methylenediphenyl diisocyanate.

16. The method according to claim 1, wherein said at least one liquid compound comprises at least 98.5 wt. % 4,4'-methylenediphenyl diisocyanate.

17. The method according to claim 1, wherein said at least one liquid compound comprises at least 97 wt. % 4,4'-methylenediphenyl diisocyanate, and has a maximum hydrolyzable chlorine content of 100 ppm as determined by ASTM D4663-10.

18. The method according to claim 1, wherein said at least one liquid compound is added above an uppermost separation element of the distillation column from an external device for storing.

19. The method according to claim 1, wherein said at least one liquid compound is recirculated from a storage tank for storing the purified 4,4'-methylenediphenyl diisocyanate, such that a ratio of an amount of recirculated 4,4'-methylenediphenyl diisocyanate to an amount of 4,4'-methylenediphenyl diisocyanate newly fed to the storage tank ranges from 0.05 to 0.4.

20. A method for purifying 4,4'-methylene diphenyl diisocyanate, the method comprising purifying a mixture by distillation through a distillation column, such that a first gaseous stream comprising the mixture contacts at least one liquid compound within the distillation column, to obtain a second gaseous stream at a top of the distillation column, which is removed to obtain purified 4,4'-methylene diphenyl diisocyanate, wherein:
the mixture comprises 4,4'-methylenediphenyl diisocyanate having a hydrolyzable chlorine content of greater than 100 ppm as determined by ASTM D4663-10;
the second gaseous stream comprises the purified 4,4'-methylenediphenyl diisocyanate having a maximum hydrolyzable chlorine content of 100 ppm as determined by ASTM D4663-10; and
wherein said distillation column comprises ordered packing elements and wherein said first gaseous stream is fed into said distillation column at a point below said ordered packing elements; and
said first gaseous stream is taken off as a side stream from a first column, and a product obtained from a bottom phase of said distillation column is recirculated to said first column,
wherein said at least one liquid compound comprises at least 97 wt. % 4,4'-methylenediphenyl diisocyanate, and has a maximum hydrolyzable chlorine content of 100 ppm as determined by ASTM D4663-10;
said at least one liquid compound is added above an uppermost separation element of the distillation column from an external device for storing; and
said at least one liquid compound is recirculated from a storage tank for storing the purified 4,4'-methylenediphenyl diisocyanate, such that a ratio of an amount of recirculated 4,4'-methylenediphenyl diisocyanate to an amount of 4,4'-methylenediphenyl diisocyanate newly fed to the storage tank ranges from 0.05 to 0.4.

21. The method according to claim 1, wherein said at least one liquid compound is recirculated from a storage tank for storing the purified 4,4'-methylenediphenyl diisocyanate, such that a ratio of an amount of recirculated 4,4'-methylenediphenyl diisocyanate to an amount of 4,4'-methylenediphenyl diisocyanate newly fed to the storage tank ranges from 0.05 to 0.4 and
wherein a ratio of said at least one liquid compound to said first gaseous stream SAT [w/w] is 0.01 to 2.0.

22. A method for purifying 4,4'-methylene diphenyl diisocyanate, the method comprising purifying a mixture by distillation through a distillation column, such that a first gaseous stream comprising the mixture contacts at least one liquid compound within the distillation column, to obtain a second gaseous stream at a top of the distillation column, which is removed to obtain purified 4,4'-methylene diphenyl diisocyanate, wherein:
the mixture comprises 4,4'-methylenediphenyl diisocyanate having a hydrolyzable chlorine content of greater than 100 ppm as determined by ASTM D4663-10;
the second gaseous stream comprises the purified 4,4'-methylenediphenyl diisocyanate having a maximum hydrolyzable chlorine content of 100 ppm as determined by ASTM D4663-10; and
wherein said distillation column comprises ordered packing elements and wherein said first gaseous stream is fed into said distillation column at a point below said ordered packing elements; and
said first gaseous stream is taken off as a side stream from a first column, and a product obtained from a bottom phase of said distillation column is recirculated to said first column,
wherein said at least one liquid compound comprises at least 97 wt. % 4,4'-methylenediphenyl diisocyanate, and has a maximum hydrolyzable chlorine content of 100 ppm as determined by ASTM D4663-10;

said at least one liquid compound is added above an uppermost separation element of the distillation column from an external device for storing; and said at least one liquid compound is recirculated from a storage tank for storing the purified 44-methylenediphenyl diisocyanate, such that a ratio of an amount of recirculated 4,4'-methylenediphenyl diisocyanate to an amount of 4,4'-methylenediphenyl diisocyanate newly fed to the storage tank ranges from 0.05 to 0.4 and wherein a ratio of said at least one liquid compound to said first gaseous stream S:V [w/w] is 0.01 to 2.0.

* * * * *